United States Patent [19]

Mestroni et al.

[11] 4,414,417
[45] Nov. 8, 1983

[54] PROCESS FOR THE CATALYTIC REDUCTION OF UNSATURATED KETONES

[75] Inventors: Giovanni Mestroni; Grazia Zassinovich; Annamaria Camus, all of Trieste, Italy

[73] Assignee: Montedison, S.p.A., Milan, Italy

[21] Appl. No.: 335,744

[22] Filed: Dec. 30, 1981

Related U.S. Application Data

[63] Continuation of Ser. No. 226,381, Jan. 19, 1981, abandoned.

[30] Foreign Application Priority Data

Jan. 23, 1980 [IT] Italy ............................. 19391 A/80

[51] Int. Cl.$^3$ ............................................. C07C 45/62
[52] U.S. Cl. ..................................... 568/315; 568/347
[58] Field of Search ......................... 568/315, 347, 391

[56] References Cited

U.S. PATENT DOCUMENTS

| | | | |
|---|---|---|---|
| 2,560,361 | 7/1951 | Morrill et al. | 568/391 |
| 3,458,547 | 7/1969 | Coffey | 568/391 |
| 4,041,083 | 8/1971 | Gradeff et al. | 568/347 |

OTHER PUBLICATIONS

Trocha-Grimshaw et al., J. Chem. Soc. Chem. Comm., p. 544, (1967).
Rigen et al., J. Org. Chem., vol. 37, pp. 1832–1833, (1972).
Gullatti et al., J. Chem. Soc. (C), pp. 2652–2656, (1971).
Sasson et al., J. Org. Chem., vol. 40, pp. 1887–1897, (1975).
Padwa et al., Tetra Letters, #45, pp. 4083–4086, (1975).
Svoboda et al., Coll. Czech. Chem. Comm., vol. 42, pp. 2177–2181, (1977).

*Primary Examiner*—James H. Reamer
*Attorney, Agent, or Firm*—Morgan, Finnegan, Pine, Foley & Lee

[57] ABSTRACT

This invention relates to a process for the reduction of α-,β-unsaturated linear homo- and heterocyclic ketones by a transfer of hydrogen from an alcohol donor to said unsaturated ketone. The alcohol donor must be unsubstituted or substituted with an inert group. Also the alcohol donor may be a primary or secondary alcohol or a glycol. The process is a catalytic one and is carried out in the presence of complexed iridium and rhodium catalysts of the following formulae:

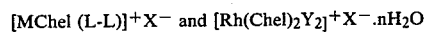

(II)          (III)

wherein:
M is selected from Ir and Rh;
Chel represents a kelating bidentate nitrogenous compound;
L—L represents a molecule of a preferably not conjugated diolefin, or two molecules of a mono-olefin;
X$^-$ represents an anion selected from among: Cl$^-$, Br$^-$, J$^-$; PF$_6^-$, BF$_4^-$, ClO$_4^-$, B(C$_6$H$_5$)$_4^-$;
Y is a halogen, preferably it is Cl or Br;
n is an integer from 0 to 3, and in the presence of a compound selected from among mineral alkalis and tertiary amines at a temperature ranging from about 20° C. to the boiling temperature of the reaction mass, in an inert atmosphere.

12 Claims, No Drawings

PROCESS FOR THE CATALYTIC REDUCTION OF UNSATURATED KETONES

This is a continuation, of application Ser. No. 226,381 filed Jan. 19, 1981 now abandoned.

The products thus obtained are represented respectively by the saturated ketone and by the alcohol or glycol reduced to aldehyde or ketone, and are used as intermediates for organic syntheses in the field of fine chemicals.

The products obtained by this invention consist respectively of the hydrogenated saturated ketone and of the alcohol or glycol dehydrogenated to ketone or to aldehyde.

This invention, as a matter of fact, although being specifically described as directed to the preparation of saturated ketones according to the above indicated technique, may, obviously be considered to be effective for obtaining ketone compounds (aldehydes or ketones) from alcohols or glycols.

These compounds can be usefully employed in a wide field of industrial applications. In fact they represent active intermediates for organic syntheses in general, with particular possibilities in the field of fine chemicals.

For many of these compounds there is a literature evidence of their industrial application. Thus, for instance, it is possible to prepare from vicinal dioles as hydrogen donors, $\alpha$-di-ketones which are valuable precursors of acetylenes and dioxymes.

BACKGROUND OF THE INVENTION

Methods are known for the preparation of saturated ketones by the catalytic transfer of a hydrogn atom from a primary or secondary alcohol molecle or from a glycol to a molecule of an $\alpha$-, $\beta$-unsaturated ketone.

The reaction results more or less shifted in the desired direction depending on the catalyst used, on the parametric conditions, etc. In general, it is best operated by using isopropanol as the alcohol donor, due to facility of separating the acetone deriving from de-hydrogenation. Nevertheless, the catalytic activity turns out to be rather low and the regio-selectivity insufficient.

Therefore, there were studied different catalytic systems that will allow to operate in a homogeneous phase. They are essentially based on the use of complexes of transition metal of Group VIII, amongst which the most studied are those derived from iridium and from ruthenium.

Thus, there have been suggested complex catalysts of the formula:

$IrHCl_2$, $(DMSO)_3$ wherein DMSO=dimethylsulphoxide: $RuCl_2=(C_6H_5)_3$, operating in an acid (HCl), neutral or alkaline or definitely alkaline medium respectively.

Generally, the primary alcohols like isopropanol are used as alcohol donors. With ruthenium catalyst benzyl alcohol is a preferred alcohol donor.

In general, however, the activity or the stereoselectivity obtained in the described substrate is not high. This is an undesirable drawback since the reaction, as previously explained, is selectively directed to yield fine chemical compounds for which the steric aspect is of the utmost importance.

Furthermore the catalyst described hereinabove provide in general unsatisfactory reaction rates no doubt lower (even of the order of 100 times), and for the iridium catalysts even $10^4$ times, than the ones achievable by the use of the catalysts according to this invention, which later, therefore, ensure aspects of a more pronounced industrial applicativity.

OBJECTS OF THE INVENTION

An object of the invention is to overcome the undesirable drawbacks in prior art methods wherein iridium and rhodium complex catalysts of the type described hereinabove which do not exhibit a satisfactory selectivity or wherein such catalysts are used in hydrogenation reactions with gaseous $H_2$.

Thus, an object of this invention is that of providing a method for the catalytic reduction of linear, homo- and heterocyclic, $\alpha$-, $\beta$-unsaturated ketones to the corresponding saturated ketones with iridium and rhodium complexes wherein such method is simple and economic, and particularly selective, starting from alcohols or glycols that are dehydrogenated to the corresponding ketones and aldehydes.

These and still other objects, which will appear mor clearly to the skilled in the art by the description which follows:

GENERAL DESCRIPTION OF THE INVENTION

According to this invention, the preparation of saturated ketones from linear homo- and heterocyclic $\alpha$-, $\beta$-unsaturated ketones as hydrogen acceptors, by the catalytic transfer of hydrogen from alcohol or glycol donors, which are dehydrogenized to ketones or aldehydes, using particular iridium and rhodium complexes, results particularly effective due to the selectivity of the reaction and the yields obtainable.

The complex iridium and rhodium catalysts used according to this invention, are compounds quite known in themselves and described as posessing catalytic capabilities in hydrogenation reactions, namely, in reactions employing molecular hydrogen as a hydrogenating agent. This technology has, however, no connection with the one adopted in this invention.

More particularly, it has been found that the invention may be realized by providing a process for the transfer of hydrogen from alcohols to linear, homo- and heterocyclic $\alpha$-, $\beta$-unsaturated ketones, catalyzed by iridium and rhodium complexes, the process being characterized in that an aliphatic, alicyclic, aromatic, primary or secondary alcohol or glycol is made to react with a ketone of formula (I):

wherein R and R' represent, indifferently, a hydrogen atom or a hydrocarbyl group while R" is a hydrocarbyl, having up to 30 carbon atoms, optionally substituted; R and R', R and R" may also be linkable with each other according to homo- or heterocycles; in the presence of a complex catalyst or iridium or rhodium selected from amongst the ones having the formulae:

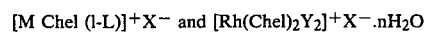

wherein:
M is selected from Ir and Rh;

Chel represents bidentate nitrogenous compound having a chelating action;

L-L represents the molecule of a preferably non-conjugated diolefin or two molecules of a monoolefin;

$X^-$ represents an anion selected from amongst: $Cl^-$, $Br^-$, $J^-$, $PF_6^-$, $BF_4^-$, $ClO_4^-$, $B(C_6H_5)_4^-$;

Y represents a halogen, preferably Cl, Br;

n is an integer from 0 to 3, at a temperature ranging from about 20° C. and the boiling temperature of the reaction mass, in an inert atmosphere and in the presence of mineral alkalis or of tertiary amines.

As substituting groups for R, R' and R" there may be cited esters, amides, alcoxy, etc.

Usually the reaction is conducted in the absence of actual solvents, the alcohol or glycol in excess also acting as a solvent. At any rate, the reaction is consistent with the conventional inert solvents like toluene, benzene, methanol, $H_2O$ etc., also in admixture.

The catalysts are used, as previously illustrated, in the presence of small amounts of mineral alkalis, preferably selected from amongst: NaOH, KOH, LiOH, $NaHCO_3$, used in a molar ratio preferably ranging from about 0.1 to 200 with respect to one mol of catalyst.

As an alternative, there may be used tertiary amines such as: triethylamine, dimethyl-benzylamine, etc.

The choice of the optimum ratio of the mineral alkali or of the amine to the Ir or Rh catalyst used, is of considerable weight for selective purposes in directing the transfer of the hydrogen towards the obtention fo the corresponding ketone.

Such a choice can be made in accordance with the nature of the substratum, of the catalyst and of the mineral alkali or of the amine, etc., used.

Better results may be obtained by subjecting the rhodium catalyst of formula (III) to a preliminary heating "in situ", namely, in the alcohol donor or in the solvent before introducing the α-, β-unsaturated ketone, in the presence of the above-mentioned alkalis or tertiary amines, and for stretches of times ranging from a few minutes to about 1 hour. In like manner, the catalysts of formula (II) provide the maximum catalytic activity in their turn, if, before undergoing said heating, they are subjected to activation by oxidation in the air and/or in molecular oxygen or in $H_2O_2$, etc. This is actually a preferred but not indispensable procedural way; for instance if the olefine is 1,5-hexadiene, such procedure is even superflueous.

The reaction may be schematically represented by the following equation:

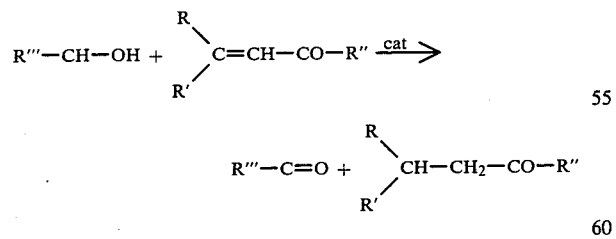

wherein the symbols R, R' and R" have the meaning, already previously indicated, and R''' represents the rest of a primary or secondary alcohol as hereinabove defined. A similar course is taken by the reaction in the case of the use of glycols.

The reaction is selectively shifted in the preferred direction, depending on the parameters (i.e. temperature, catalysis, etc.) and on the conduction conditions, for instance by substracting a proper chemical species, etc.

The iridium and rhodium complexes used as catalysts according to this invention, are in their turn prepared according to known or conventional techniques.

For instance, the complex of type (II) of the formula [Rh Chel (1,5-hexadiene)] $PF_6$ wherein the chelating compound is selected from amongst: 2,2'-dipyridyl(bipy), 4,4'-dimethyl-2,2'-dipyridyl, 1,10-phenanthroline, 5,6-dimethyl-1,10-phenanthroline, etc., can be synthetized by addition of the chelating compound to a deaerated methanolic solution of $[Rh-hexadiene-Cl]_2$, followed by the optional treatment with a salt containing the desired anion other than chlorine.

The complex of the formula $[Rh (Chel)_2Cl_2]Cl$ of Type (III) wherein the chelating compound is, for instance, 2,2'dipyridyl(bipy), can be prepared starting from an aqueous solution of $RhCl_3.3H_2O$ to which a hot ethanol solution of the chelating compound, in a molar ratio of 1:2 is added. The resulting reaction mixture heated to 60° C., is added with a small amount of chlorohydrated hydrazine and is heated to boiling temperature for 3 minutes.

After cooling of the solution there precipitates the desired product in the form of a yellow solid.

In like manner, the iridium complex of the formula [Ir Chel(L-L)]Cl of type (II), wherein the chelating compound is, for instance, 3,4,7,8-tetramethyl-1,10-phenanthroline and L-L is 1,5-cyclooctadiene (COD), can be prepared starting from a solution of $[IrCODCl]_2$ in methylene chloride by the addition of a slight excess of the chelating compound and by the successive precipitation with ethyl ether. These are known or conventional techniques.

As illustrated before, the complex iridium and rhodium catalysts used according to this invention are of the formulas (II) and (III), in which more particularly, the nitrogenous bidentate chelating compound (Chel), is preferably selected from amongst: 2,2'-dipyridyl (bipy), 4,4'-dimethy-2,2'-dipyridyl, 1,10-phenanthroline, 5,6-dimethyl-1,10-phenanthroline, 4,7 dimethyl-1,10-phenanthroline, 3,4,7,8-tetramethyl-1,10-phenanthroline.

Or is it possible to employ the chelating compounds of formulas (IV) and (V), obtained from pyridin-2-aldehyde or from 2-acyl-pyridin, also substituted (by alkyls, alkoxyls), by condensation with alkylaryl primary amines, hydrazines, also N,N-substituted, hydroxylamine (IV), or by condensation of alpha-diketones or alpha-dialdehydes, such as diacetyl and glyoxal, with the abovesaid amines, etc. (V):

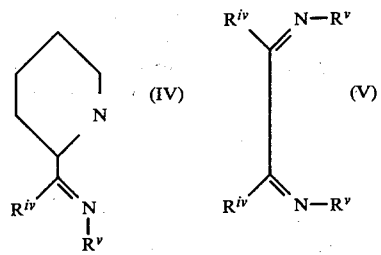

in which groups $R^{iv}$, like or unlike one another, are selected from amongst H, alkyls and aryls, and groups $R^v$, like or unlike one another, are selected from amongst OH, $NH_2$, alkyls and aryls, all having up to 30 carbon atoms, also containing functional groups such as carboxyl, ester, amide groups, etc.

Particularly effective chelating compounds, in this regard, have proved to be the chelating compounds of formulas (IV) and (V) in which groups R$^v$, like or unlike one another, are groups as defined hereinbefore containing chiral centres, i.e, at least an optically active atom, such as for example:

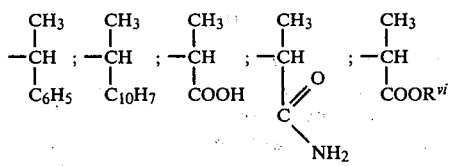

in which R$^{vi}$=CH$_3$, iso C$_3$H$_7$ etc. In formulas (IV) and (V) groups R$^{iv}$ and R$^v$ can be also connected with one another according to homo- or heterocycles.

The synthesis of the rhodium- and of the iridium catalysts containing the said optically active chiral chelating compounds is described, for example, in Journal of Organometallic Chemistry, 133(1977), 377–384. 2-pyridinalphenylethylimine (PPEI), 2-pyridinalnaphthylethylimine, etc. have proved to be effective chelating compounds.

Nevertheless, some terms of the abovesaid group of iridium and rhodium catalysts' containing chelating compounds of formula (IV) or (V) are to be considered as new in themselves.

The preferably non-conjugated diolefin is selected from amongst 1,5-hexadiene, norbornadiene and 1,5-cyclooctadiene; the monoolefin is cyclooctene or ethylene; anion X$^-$ has been already defined.

Finally, the catalyst according to this invention can also be prepared directly "in situ" in the reaction medium by the addition of the selected chelating compound to the halogenated olefinic complex of iridium or of rhodium; for instance to [Rh-1,5-hexadiene-Cl]$_2$ or to [Rh(cyclooctene)$_2$Cl]$_2$, there is added dipyridyl in the desired ratio and the whole is then activated as explained hereinbefore.

The catalyst, according to this invention is employed in amounts that may vary over wide range.

Advantageous results are obtained by employing for each mol of α-, β-unsaturated ketone (I) amounts of catalyst ranging from about $1 \times 10^{-2}$ to $1 \times 10^{-6}$ mols.

The complex iridium and rhodium catalysts according to this invention are used according to conventional techniques in a basic medium which is basic, as indicated above, due to mineral alkalis or for tertiary amines.

Suitable reaction media are preferably the alcoholic solutions consisting of the alcohol or of the glycol donor in excess, which acts as the reaction medium, and of a base as hereinabove defined.

The concentration of the α-, β-unsaturated ketone in the reaction mass is not critical for the purpose of a correct conduction of the reaction. Values comprised between 10 and $10^{-3}$ mols about per liter are quite effective.

The reaction is conducted according to a molar ratio between the reactants varying throughout a wide range; practically optimum results may be achieved with molar ratio values between alcohol or glycol donor and α-, β-unsaturated ketone acceptor ranging from 1:1 to 20:1 about, the alcohol or glycol in excess being used as a solving reaction medium; values near the stoichiometric value are however preferred.

The concentration of the catalyst in the reaction mass is practically comprised between $10^{-1}$ and $10^{-6}$ mols about per liter of reaction mass.

The reduction of dehydrogenation reaction according to this invention is conducted at atmospheric pressure and under an inert atmosphere such as nitrogen, argon, etc.

Temperatures ranging approximately from 20° to about 200° C. are possible up to the boiling temperature of the solution.

The ketones reducible according to the invention in particular are: benzylidene acetone, chalcone, carvone, and the 2-methyl-cyclohexene-1-one. Of course, there may also be used ketones having two hydrogenizable α-, β-unsaturated positions, such as for instance dibenzylideneacetone.

As effective aliphatic alcohol donors may be cited, for instance amongst the saturated compounds; isopropyl alcohol, ethyl alcohol, 2-butyl alcohol, benzyl alcohol, etc.; as glycol there may be mentioned the 1,2-cyclododecandiol glycol etc. Products of the commercial type are employable.

The product is then separated according to conventional techniques. Practically, it is the question of separating the solvent by distillation, while the high-boiling part consists of the desired saturated ketone generally in a quantitative amount, etc.

According to an effective embodiment of the invention, it is operated in practice as follows:

Into a reactor, fitted with suitable reactant feeding systems and thermoregulated, there are introduced the optional solvent and the alcohol or glycol donor, whereafter there is fed the desired amount of catalyst or of oxidized catalyst and of base in the proper ratios. Thereupon the catalyst is activated by heating and finally there is added the α-, β-unsaturated ketone in the pre-established ratio, in a nitrogen stream, by heating to temperature and time fixed. At the conclusion of the reaction, for instance controlled by gas-chromatography, one proceeds to the isolation of the product according to conventional techniques.

The process, thanks to the simple and mild operative conditions, results particularly advantageous.

SPECIFIC DESCRIPTION OF THE INVENTION

The present invention will no be further described in the following examples which are given, however, for merely illustrative purposes.

Just for the sake of clearness, the symbols used hereinunder are: Me=methyl; phen=phenanthrolin; "bipy" stands for: 2,2'-dipyridyl; COD=1,5-cyclooctadiene, S=substratum.

EXAMPLE 1

5.5 mg ($1 \times 10^{-5}$ mols) of [Ir(3,4,7,8(CH$_3$)$_4$phen-COD] Cl were oxidized in the air in 50 ml of isopropanol-H$_2$O (1%) and to the deaerated solution it was then additioned 0.5 ml of an aqueous solution of KOH (1.5 mg of KOH). The solution was then reflux-heated for 1 hour and was then additioned with 5 g of chalcone under a stream or Argon.

The whole was then reflux-heated for 5 minutes.

Ratios used: [s]: [cat]=2,400; [KOH]: [cat]=3% conversion=100%; % selectivity=99%.

The saturated dihydrochalcone was isolated by cold precipitation and subsequent filtering and then it was identified by IR and NMR spectrum analysis. The acetone was obtained by fractioned distillation of the reaction mixture.

EXAMPLE 2

It was operated in the same way as that followed in Example 1, by respectively using:

2.75 mg of complexed compound and 1.5 mg of KOH, in ratios [s]: [cat]=4,800; [KOH]: [cat]=6, after 45 minutes there were obtained: % conversion=93%; % selectivity=92.5%.

EXAMPLE 3

There were followed the same procedures as those of Example 1, with 2.75 mg of complexed compound and 0.75 mg of KOH. Ratios: [s]: [cat]=4,800; [KOH]:[cat]=3.

After 5 minutes there was obtained a: % conversion=94%; % selectivity=98%.

EXAMPLE 4

Operating in the same way as in Example 1, but with 1.37 mg of complexed compound and 0.75 mg of KOH with the following ratios: [s]: [cat]=9,600; [KOH]:[cat]=6, after 30 minutes there was obtained: % conversion=96%; % selectivity=97%.

EXAMPLE 5

6.5 mg ($1 \times 10^{-5}$ mols) of [Ir 4,7($CH_3$)$_2$ phen COD]$PF_6$ were oxidized in the air in 50 ml of isopropanol-$H_2O$ (1%) and to the deaerated solution were then additioned 0.5 ml of an aqueous solution of KOH (1.5 mg).

The solution was then reflux-heated for 45 minutes after which, under a stream of Argon, there were added B 5 g of chalcone. Then the solution was reflux-heated for further 45 minutes.

The ratios used were: [s]: [cat]=2,400; [KOH]:[cat]=1.5 % conversion=96%; % selectivity=99% in dihydrochalcone.

EXAMPLE 6

Operating in the same way as in Example 5 and using respectively: 3.26 mg of complexed compound and 1.5 mg of KOH, in the following ratios: [s]: [cat]=4,800; [KOH]: [cat]=3, after 60 minutes there were obtained: % conversion=92%; % selectivity=99% in dihydrochalcone.

EXAMPLE 7

6.25 mg ($1 \times 10^{-5}$ mols) of [Ir 4,4'($CH_2$)$_2$ bipy COD]$PF_6$ were oxidized in the air in 50 ml of isopropanol-$H_2O$ (1%) and to this deaerated solution were then additioned 0.5 ml of an aqueous solution of KOH (1.5 mg). The solution was then reflux-heated for 40 minutes and then additioned with 5 g of chalcone under a stream of Argon.

The whole was then reflux-heated for further 90 minutes. The ratios used were: [s]: [cat]=2,400; [KOH]: [cat]=1.5.

There were obtained: % conversion=95.5%; % selectivity=97.5% in dihydrochalcone.

EXAMPLE 8

2.84 mg of [Ir PMI (COD)]$^+$ $PF_6^-$ ($5 \times 10^{-6}$ mols). (PMI=pyridine-2-aldehyde-methylamine) were oxidized in the air in 50 ml of isopropanol.

To the deaerated solution there were then additioned 2 mg of KOH dissolved in 0.8 ml of isopropanol. The solution was then reflux-heated for 30 minutes in a nitrogen stream after which it was additioned with 2.1 g of chalcone. Then it was reflux-heated for another 150 minutes.

The ratios used were: [s]:[cat]=2,000; [KOH]:[cat]=8. There were thus obtained: % conversion=26%; % selectivity=100% in dihydrochalcone.

EXAMPLE 9

11 mg of [Ir 3,4,7,8 ($CH_3$)$_4$phen COD] Cl ($2 \times 10^{-5}$ mols) were oxidized in the air in 50 ml of isopropanol-$H_2O$ (1%) and to the deaerated solution was then additioned 0.5 ml of an aqueous solution of KOH (1.5 mg). This solution was then reflux-heated for 45 minutes whereafter it was additioned with 5 g of benzylideneacetone in a stream of Argon.

Then it was once again reflux-heated for further 24 minutes.

Ratios used: [s]:[cat]=1,700; [KOH]:[cat]=1.5. There were obtained: % conversion=85.5%; % selectivity=96% in 4-phenyl-butane-2-one.

EXAMPLE 10

By operating in the same way as in Example 9 and by using respectively: 11 mg of complexed compound and 3 mg of KOH in the following ratios: [s]:[cat]=1,700; [KOH]:[cat]=3, in 8 minutes there were obtained: % conversion=88%; % selectivity=88%.

EXAMPLE 11

Operating as in Example 9, and using respectively: 5.5 mg of complexed compound and 1.5 mg of KOH with the following ratios: [s]:[cat]=3,400; [KOH]:[cat]=3, after 10 minutes of reaction there were obtained: % conversion=93%; % selectivity=90%.

EXAMPLE 12

Operating as in Example 9 and by using respectively: 2.75 mg of complexed compound and 1.5 mg of KOH with the following ratios: [s]:[cat]=6,800; [KOH]:[cat]=6, after 15 minutes there were obtained: % conversion=93%; % selectivity=89%.

EXAMPLE 13

8.6 mg of [Ir 3,4,7,8 ($CH_3$)$_4$phen COD] B($C_6H_5$)$_4$ ($1 \times 10^{-5}$ mols) were oxidized in the air in 50 ml of isopropanol-$H_2O$ (1%) and to the deaerated solution were then added 0.5 ml of an aqueous solution of KOH (1.5 mg).

This mixture was reflux-heated for 45 minutes and it was then additioned with 5 g of benzylideneacetone under a stream of Argon. The mixture was then reflux-heated for 10 minutes thereby obtaining: % conversion=77%; % selectivity=92% in 4-phenyl-butane-2-one, with the following ratios: [s]:[cat]=3,400; [KOH]:[cat]=3.

EXAMPLE 14

10 mg of [Ir 4, 7($CH_3$)$_2$phen COD]Cl ($2 \times 10^{-5}$ mols) were oxidized in the air in 50 ml of isopropanol-$H_2O$ (1%) and to the deaerated solution there were added 0.5 ml of an aqueous solution of KOH (1.5 mg).

The solution was then reflux-heated for 45 minutes and additioned with 5 g of benzylideneacetone under a stream of Argon. Whereupon it was reflux-heated for further 80 minutes. The ratios used were: [s]:[cat] = 1,700; [KOH]:[cat] = 1.5.

Thereby were obtained: % conversion = 84.5%; % selectivity = 97% in 4-phenyl-butane-2-one.

EXAMPLE 15

6.5 mg of [Ir 4,7 $(CH_3)_2$phen COD]$PF_6$ ($1 \times 10^{-5}$ mols) were oxidized in the air in 50 ml of isopropanol-$H_2O$ (1%) and to the deaerated obtained solution there were added 0.5 ml of an aqueous solution of KOH (1.5 mg).

The solution was then reflux-heated for 30 minutes and then additioned with 5 g of benzylideneacetone in a stream of Argon. It was then reflux-heated for 70 minutes. The ratios used were: [s]:[cat] = 3,400; [KOH]:[cat] = 3.

Thereby were obtained: % conversion = 74.5%; % selectivity = 98.5% in 4-phenyl-butane-2-one.

EXAMPLE 16

12.5 mg of [Ir 4,4'$(CH_3)_2$bipy COD]$PF_6$ ($2 \times 10^{-5}$ mols) were oxidized in 50 ml of isopropanol-$H_2O$ (1%) in the air and then the deaerated solution was additioned with 0.5 ml of an aqueous solution of KOH (1.5 mg). The resulting solution was reflux-heated for 45 minutes and then, in a stream of Argon, it was additioned with 5 g of benzylideneacetone. The resulting solution was reflux-heated for further 30 minutes.

The ratios used were: [s]:[cat] = 1,700; [KOH]:[cat] = 1.5. There were obtained: % conversion = 92.5%; % selectivity = 98% in 4-phenyl-butane-2-one.

EXAMPLE 17

Operating under the same conditions as in Example 16, and using 6.25 mg of complexed compound and 1.5 mg of KOH in the respective ratios of: [s]:[cat] = 3,400; [KOH]:[cat] = 3. After 75 minutes there were obtained: % conversion = 96.5%; % selectivity = 95% in 4-phenyl-butane-2-one.

EXAMPLE 18

11 mg of [Ir 3,4,7,8$(CH_3)_4$phen COD]Cl ($2 \times 10^{-5}$ mols) were oxidized in 50 ml of isopropanol-$H_2O$ (1%) in the air, and to the deaerated solution were then added 11 mg of KOH.

The solution was reflux-heated for 20 minutes, then additioned in an Argon stream with 2 ml of carvone.

It was then reflux-heated for 5 minutes. The ratios used were: [s]:[cat] = 650; [KOH]:[cat] = 10. There were obtained % conversion = 82%; % selectivity = 90% in dihydrocarvone.

EXAMPLE 19

Operating under the same conditions as those of Example 18, and using 5.5 mg of complexed compound and 5 mg of KOH, and with ratios: [s]:[cat] = 1,300; [KOH]:[cat] = 10, there were obtained after 5 minutes: % conversion = 77%; % selectivity = 90% in dihydrocarvone.

EXAMPLE 20

Operating as in Example 18 and using 5.5 mg of complexed compound and 2.25 mg of KOH in the following ratios: [s]:[cat] = 1,300; [KOH]:[cat] = 5, after 45 minutes there were obtained: % conversion = 85%; % selectivity = 93% in dihydrocarvone.

EXAMPLE 21

11 mg of [Ir 3,4,7,8$(CH_3)_4$phen COD]Cl dissolved in 50 ml of isopropanol-$H_2O$ (1%) were treated in an Argon stream with 5 mg of KOH (0.5 ml in aqueous solution) and then reflux-heated for 30 minutes.

To this solution were then admixed 2 ml of 3-methyl-2-cyclo-hexene-1-one and the whole was thereupon reflux-heated for further 30 minutes. The ratios used were: [s]:[cat] = 880; [KOH]:[cat] = 5.

There were obtained: % conversion = 66%; % selectivity = 38% in 3-methyl-4-cyclo-hexanone.

EXAMPLE 22

Operating under the same conditions as those of Example 21, and using 5.5 mg of complexed compound and 5 mg of KOH, there were obtained after 30 minutes of reaction: % conversion = 67%; % selectivity = 41% in 3-methylcyclo-hexanone, with the following ratios: [s]:[cat] = 1,760; [KOH]:[cat] = 10.

What is claimed is:

1. A process for the reduction by the transfer of hydrogen from alcohols to linear, homo- and hetero-cyclic α-,β-unsaturated ketones, said reduction being catalyzed by iridium complexes, characterized in that an aliphatic, alicyclic primary or secondary alcohol is reacted with a ketone selected from the group consisting of benzylideneacetone, dibenzylideneacetone, chalcone, carvone and 2-methylcyclohexene-1-one in the presence of a complex catalyst of iridium having the formula:

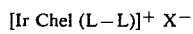

[Ir Chel (L—L)]$^+$ X$^-$ wherein:
Chel is a chelating bidentate nitrogenous compound selected from the group consisting of 2,2'-dipyridyl; 4,4'-dimethyl-2,2'-dipyridyl; 1,10-phenantroline; 5,6-dimethyl-1,10-phenantroline; 4,7-dimethyl-1,10-phenantroline and 3,4,7,8-tetramethyl-1,10-phenantroline;

L-L is a molecule of an unsubstituted non-conjugated acylic or cyclic diolefin, or two molecules of an unsubstituted acyclic or cyclic mono-olefin;

X represents an anion selected from the group consisting of Cl$^-$, Br$^-$, I$^-$, $PF_6^-$, $BF_4^-$, $ClO_4^-$ and $B(C_6H_5)_4$;

and in the presence of small amounts of a mineral alkali at a temperature ranging from about 20° C. to the boiling temperature of the reaction mass, in an inert atmosphere.

2. A process according to claim 1, characterized in that the mineral alkali is a mineral alkaline compound selected from the group consisting of NaOH, KOH, LiOH, $NaHCO_3$, in a molar ratio to the catalyst of from about 0.1 to 200 mols per 1 mol of catalyst.

3. A process according to claim 1, characterized in that said process is conducted in a medium selected from the group consisting of the alcohol in excess and a compound selected from the group consisting of toluene, benzene, methanol, and water, optionally in admixture with each other.

4. A process according to claim 1, characterized in that the diolefin is a non-conjugated diolefin selected from the group consisting of 1,5-hexadiene, norbornadiene and 1,5-cyclo-octadiene, and that the monoolefine is selected from the group consisting of cyclooctene and ethylene.

5. A process according to claim 1, characterized in that for 1 mol of α-,β-unsaturated ketone (1) from $1\times10^{-2}$ to $1\times10^{-6}$ about mols of catalyst are employed.

6. A process according to claim 1, characterized in that the molar ratio of the reagents, alcohol or glycol donor to the α-,β-unsaturated ketone (1) approximately ranges from 1:1 to about 20:1, but preferably it is the stoichiometric one.

7. A process according to claim 1, characterized in that the concentration of the α-,β-unsaturated ketone (I) in the reaction medium approximately ranges from 10 to $10^{-3}$ mols per about 1 liter.

8. A process according to claim 1, characterized in that the catalyst concentration approximately ranges from $10^{-1}$ to $10^{-6}$ mols per liter of reaction mass.

9. A process according to claim 1, characterized in that the alcohol donor is selected from the group consisting of ethyl alcohol, isopropyl alcohol, 2-butyl alcohol and benzyl alcohol.

10. A process according to claim 1, characterized in that the alcohol donor is 1,2-cyclododecandiol.

11. A process according to claim 1 or 2 characterized in that the catalyst of formula:

$$[\text{Ir Chel (L-L)}]^+ X^-$$

wherein the symbols have the meaning, specified in claim 1, is activated by oxidation with oxygen or a source thereof and by successive heating in the reaction medium in the presence of the mineral alkaline compound.

12. A process according to the claims 1 or 2 characterized in that the complex catalyst of iridium is prepared "in situ" in the reaction medium by adding the chelating compound to the halogenated olefinic complex of iridium.

* * * * *

UNITED STATES PATENT AND TRADEMARK OFFICE
CERTIFICATE OF CORRECTION

PATENT NO. : 4,414,417
DATED : NOVEMBER 8, 1983
INVENTOR(S) : GIOVANNI MASTRONI, GRAZIA ZASSINOVICH and
ANNAMARIA CAMUS It is certified that error appears in the above-identified patent and that said Letters Patent is hereby corrected as shown below:

COLUMN 7, line 37 - delete "B".

Signed and Sealed this

Thirtieth Day of October 1984

[SEAL]

Attest:

GERALD J. MOSSINGHOFF

*Attesting Officer*     *Commissioner of Patents and Trademarks*